United States Patent [19]

Falcone et al.

[11] Patent Number: 5,263,929
[45] Date of Patent: Nov. 23, 1993

[54] PORTABLE FLUID ADMINISTRATION CONTAINER WITH INTEGRAL HEAT EXCHANGER

[75] Inventors: Robert E. Falcone; James F. Davis, both of Columbus, Ohio

[73] Assignee: Normothermic Technologies, Inc., Columbus, Ohio

[21] Appl. No.: 751,396

[22] Filed: Aug. 28, 1991

[51] Int. Cl.⁵ .............................................. A61M 37/00
[52] U.S. Cl. ...................................... 604/89; 604/113; 604/416; 126/263 DB
[58] Field of Search .......................... 128/399–403, 128/DIG. 24; 604/113, 114, 82–91, 408, 410, 416; 126/263

[56] References Cited

U.S. PATENT DOCUMENTS

| | | | |
|---|---|---|---|
| 2,541,736 | 2/1951 | Alexander | 126/263 |
| 2,907,173 | 10/1959 | Robbins | 126/263 |
| 3,023,750 | 3/1962 | Baron | 604/141 |
| 3,175,558 | 3/1965 | Caillouette | 128/403 |
| 3,865,117 | 2/1975 | Perry, III | 128/403 |
| 3,950,158 | 4/1976 | Gossett | 128/403 |
| 3,951,127 | 4/1976 | Watson et al. | 128/399 |
| 3,976,049 | 8/1976 | Yamashita et al. | 126/263 |
| 3,980,070 | 9/1976 | Krupa | 128/403 |
| 4,077,390 | 3/1978 | Stanley et al. | 126/263 |
| 4,177,816 | 12/1979 | Torgeson | 128/400 |
| 4,334,519 | 6/1982 | Cieslak et al. | 128/399 |
| 4,379,453 | 4/1983 | Baron | 604/145 |
| 4,484,920 | 11/1984 | Kaufman et al. | 604/87 |
| 4,522,640 | 6/1985 | Jagoe, III | 128/403 |
| 4,531,941 | 7/1985 | Zasuwa | 604/113 |
| 4,572,158 | 2/1986 | Fiedler | 126/263 |
| 4,623,333 | 11/1986 | Fried | 604/113 |
| 4,678,460 | 7/1987 | Rosner | 604/113 |
| 4,680,445 | 7/1987 | Ogawa | 604/114 |
| 4,705,505 | 11/1987 | Fried | 604/80 |
| 4,735,609 | 4/1988 | Comeau et al. | 604/114 |
| 4,779,609 | 10/1988 | Oblon | 126/263 |
| 4,780,117 | 10/1988 | Lahey et al. | 126/263 |
| 4,856,651 | 8/1989 | Francis, Jr. | 128/403 |
| 4,934,336 | 6/1990 | White | 126/263 |
| 5,042,455 | 8/1991 | Yue et al. | 126/263 |

FOREIGN PATENT DOCUMENTS

| | | | |
|---|---|---|---|
| 56-80245 | 7/1981 | Japan | 128/399 |
| 59-71384 | 4/1984 | Japan | 604/113 |
| 60-39309 | 9/1985 | Japan | 128/399 |
| 8706825 | 11/1987 | World Int. Prop. O. | 128/399 |

*Primary Examiner*—C. Fred Rosenbaum
*Assistant Examiner*—Mark Bockelman
*Attorney, Agent, or Firm*—Roger A. Gilcrest

[57] ABSTRACT

The present invention is addressed to providing an infusion administration container which is effective in establishing about a normothermic temperature of a physiologic solution for its infusion into an animal, such as a human medical patient. The infusion administration container comprises an upper flexible bladder adapted to contain at least one first chemical agent and a first lower flexible bladder adapted to contain at least one second chemical agent. These first and second chemical agent(s), when combined, result in an exothermic reaction. A passageway interconnects the upper bladder and first lower bladder with manually openable closure means disposed within the passageway to separate the chemical agents until the closure means is opened. A second lower flexible bladder, adapted to contain an administrable physiologic fluid, is disposed in heat-exchange relationship with the first lower bladder. The passageway is dimensioned such that when the closure means is opened, the first chemical agent(s) flows into the first lower flexible bladder at a rate sufficient so the resulting exothermic reaction generates sufficient heat to maintain the physiologic fluid within a normothermic temperature range for its infusion into the desired patient. The present invention also includes a method of maintaining a physiologic fluid within a normothermic temperature range for its infusion into a desired patient.

19 Claims, 5 Drawing Sheets

PORTABLE FLUID ADMINISTRATION CONTAINER WITH INTEGRAL HEAT EXCHANGER

BACKGROUND OF THE INVENTION

The present invention relates to the warming of physiologic fluids for infusion, such as is done in the treatment of humans or other animals for hypovolemic shock by infusion of physiologic solutions into the body. The invention more particularly relates to a infusion administration device which is capable of warming the physiologic solution to about a normothermic temperature for infusion. Also part of the present invention is a method of bringing a physiologic fluid to within and/or maintaining such a fluid within a normothermic temperature range for its administration into a human or other animal.

Treatment of shock (e.g. hypovolemic shock) can require volumetric fluid replacement and maintenance of a normothermic temperature in vital organs of an animal (e.g. human) body. In order to resuscitate a victim of shock, secondary to traumatic hemorrhage for example, physiologic solutions including blood products, synthetic colloids, and crystalloids, must be infused into the body. These physiologic solutions presently are introduced through a multitude of venipunctures cannulated with 18-gauge or larger internal diameter catheters. The infused physiologic solutions also should be warmed to about a normothermic temperature in order to maintain normothermic temperature in the vital organs of the body and prevent transfusion-induced hypothermia.

In clinical settings, present methods of fluid administration achieve rapid infusion rates when required, and achieve careful heating of the infusion fluid to a normothermic temperature. Various types of such apparatus are disclosed in U.S. Pat. Nos. 3,023,750, 4,177,816, 4,379,453, 4,531,941, 4,623,333, 4,678,460, 4,705,505, 4,735,609, 4,934,336, which are hereby incorporated by reference.

The need for warming of the infused products can be seen, for instance, in the administration of cold fluids such as banked blood which is often stored in a refrigerated environment at a temperature of about 4° C. Patients who receive as little as two units of such cold banked blood tend to become hypothermic. The first major organ to be exposed to the stream of cold bank blood is the heart. Heart rate, blood pressure, cardiac output, and coronary blood flow all fall progressively as body temperature drops; thus, the need exists for warming of the infused products prior to their infusion.

In non-clinical settings, the physiologic solutions are subjected to even more severe conditions. Such non-clinical settings include emergency vehicles and ambulances in the field, medical helicopters in the field, and the like. Depending upon the climate, the physiologic solutions may be subjected to cold temperatures due to the environment. Also, conventional methods for warming of the physiologic solutions cannot readily be implemented away from the emergency vehicle as a power supply is not readily available. Moreover, for blood products, a maximum temperature of 42° C. must not be exceeded; otherwise, the blood cells can hemolyze with resultant disqualification of such blood products for their infusion. Moreover, non-blood products normally will be stored at ambient temperature as refrigeration is not required for preservation purposes. However, there is still a need in non-clinical settings to adjust and/or maintain the temperature of physiologic fluids prior to their infusion into the body.

Other applications for the present invention include the administration of blood, blood products, or any of several non-blood materials or products in clinical or emergency settings, beyond those described above.

SUMMARY OF THE INVENTION

The present invention is directed toward providing an infusion administration container which is effective in establishing and maintaining a physiologic fluid within a normothermic temperature range for its infusion into a human or other animal patient. The infusion administration container of the present invention may be made to be disposable and/or portable as desired, through the use of appropriate materials. In its most general form, the container of the present invention comprises an upper flexible bladder adapted to contain at least one first chemical agent, a first lower flexible bladder adapted to contain at least one second chemical agent, and a second lower flexible bladder adapted to contain an administrable physiologic fluid, and disposed in heat-exchange relationship with the first lower bladder. The first lower bladder preferably is contained within the second lower bladder for more efficient heat transfer.

A passageway interconnects the upper and first lower bladders with manually openable closure means disposed within the passageway to separate the chemical agents until the closure means is opened. This may be provided, for instance, by any appropriate valve means known in the art. The passageway is dimensioned such that when the closure means is opened, the first chemical agent(s) flows into the first lower flexible bladder at a rate sufficient so the resulting exothermic reaction with the second chemical agent(s) generates sufficient heat to sufficiently quickly establish and/or maintain the physiologic fluid within a normothermic temperature range for its infusion into the patient.

By "maintain" is meant that the temperature of the infusible material will be within the normothermic range for a period of time adequate for administration of such material. As used herein the term normothermic range means a temperature range appropriate to avoid harm to the living organism into which a physiologic fluid is being infused; generally a range including the normal body temperature range of the living organism in question.

The materials used to make the infusion administration container of the present invention may be selected from any liquid- and air-tight material appropriate for use in the handling of the desired physiologic fluid to be administered, and for containing the chemical agents and their reaction product used to generate the exothermic reaction. These materials may include commonly used polymeric materials, such as polyvinylchlorides (PVC). It is preferred that the materials be chosen to make the container easily portable and/or more economically disposable.

The first chemical agent(s) and the second chemical agent(s), are to be selected such that, when combined, they give rise to an exothermic reaction. The chemical agents used for the first and second chemical agents in the present invention may be selected from any combination of reactants that give rise to an exothermic reaction upon mixing. The chemical agents used in the present invention are preferably selected from materials safe for use in association with the warming of administrable physiologic fluids and for use with their containers. Otherwise, the amount and type of the chemical agents used need only be selected so as to yield a sufficient amount of heat upon reaction to warm the intended amount of the particular physiologic fluid to be administered. The first and second chemical agents will typically be in solid or liquid (i.e. pure, solution or suspension) form, although it is preferred that the first chemical agent(s) be in liquid form to facilitate transport to the first lower bladder. It is also preferred that the first and second chemical agents when mixed be in liquid form to better facilitate the transfer of heat from the chemical agents to the physiologic fluid.

Combinations of materials used as the first and second chemical agents (which is immaterial) include, among many other possible categories of reactants, combinations such as: (1) water and a hydratable organic or inorganic compound (e.g. magnesium sulfate); or (2) at least one acid and at least one base.

As used herein, the term "physiologic fluid" or "fluid" shall mean any fluid which may be used in the present invention for infusion into an animal, including, without limitation, any fluid, solution, suspension, emulsion or combination of any of the foregoing, appropriate for infusion into the subject animal or human medical patient for the desired purpose. Such fluids may include blood and blood products, serum, artificial physiologic fluids such as synthetic colloids and crystalloids, saline solutions, dextrose solutions, or solutions or suspensions containing medications or otherwise having a therapeutic effect.

The corresponding method for establishing and/or maintaining a physiologic fluid within a normothermic temperature range for its infusion into an animal, such as a human medical patient, comprises providing an infusion administration container which comprises an upper flexible bladder containing at least one first chemical agent, a first lower flexible bladder containing at least one second chemical agent. The first and second chemical agents when combined bring about an exothermic reaction; there being a passageway interconnecting the upper and first lower bladders with manually openable closure means disposed within the passageway to separate the first and second chemical agents until said closure means is opened, and a second lower flexible bladder containing an administrable, physiologic fluid, and being in heat exchange relationship with the first lower bladder. The initial temperature of stored blood or blood products is typically in the range of 0 to 30 degrees Centigrade, while non-blood materials may be stored within this temperature range or at higher temperatures, such as room temperature.

Next, the closure means is opened. The passageway is dimensioned such that the first chemical agent(s) flows into the first lower flexible bladder at a rate sufficient so that its resulting exothermic reaction with the second chemical agent(s) generates sufficient heat to bring the physiologic solution to within a normothermic temperature range and/or maintain it in this range for its infusion into the patient. The administration container is preferably agitated (such as through inversion, shaking or squeezing) upon the opening of the closure means and/or during the infusion operation to provide adequate mixing of the first and second chemical agents.

Advantages of the present invention include the ability to establish and/or maintain administrable physiologic solutions at about a normothermic temperature for infusion into a human or animal patient at locations remote from controlled clinical settings or in clinical settings in which conventional warming techniques are not practical. Another advantage is to provide a portable infusion administration container which is disposable, i.e. inexpensive in cost. These and other advantages will be readily apparent to those skilled in the art based upon the disclosure contained herein.

The drawings will be described in detail in connection with the following detailed description of a few embodiments of the invention.

DETAILED DESCRIPTION OF THE INVENTION

The following is a description of the preferred embodiment of the present invention (with an alternative embodiment), which also represents the best mode contemplated by the inventors.

Figure 2:
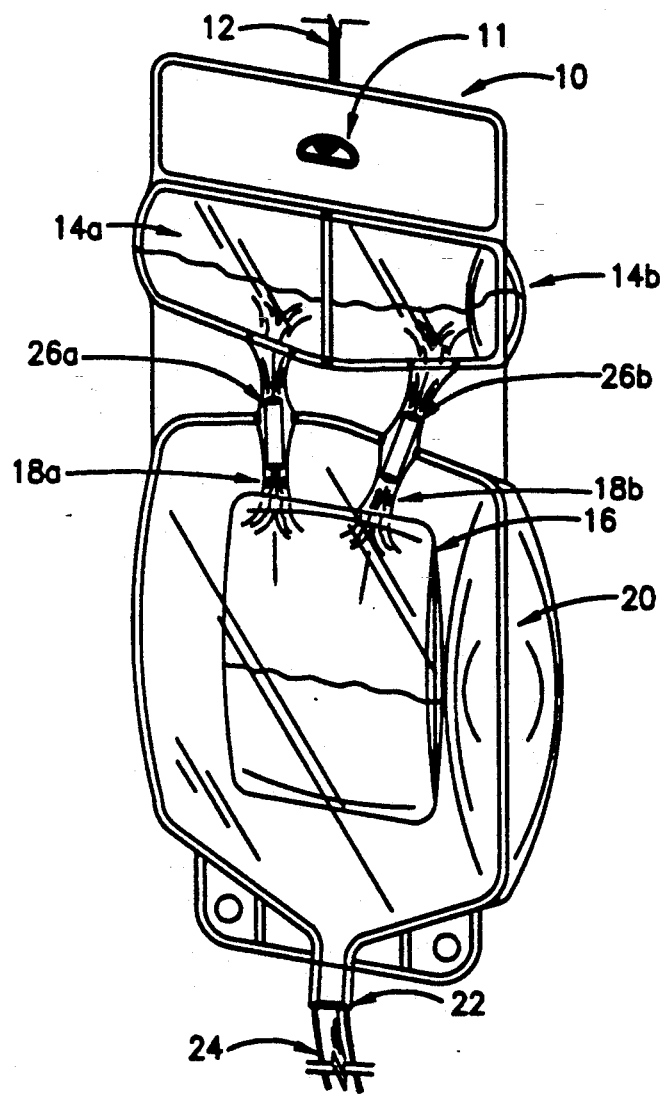
FIG. 2 is a perspective view of one embodiment of the infusion administration container of the present invention.
Figure 3:
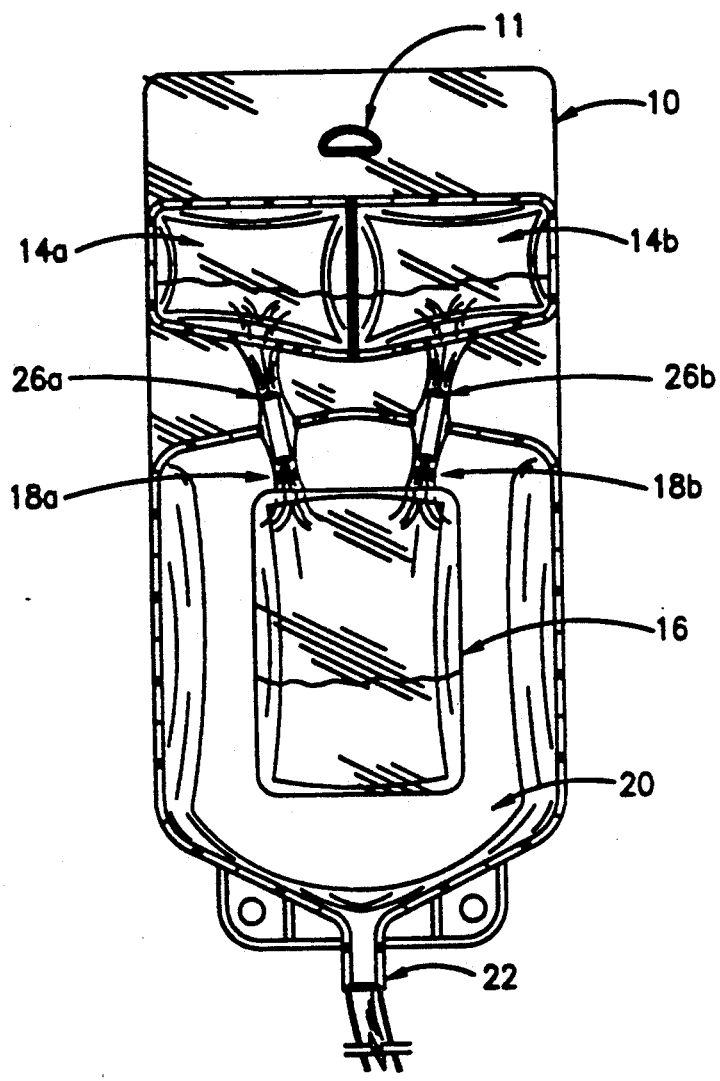
FIG. 3 is a side cross-sectional elevational view of the infusion administration container of FIG. 2.
Figure 4:
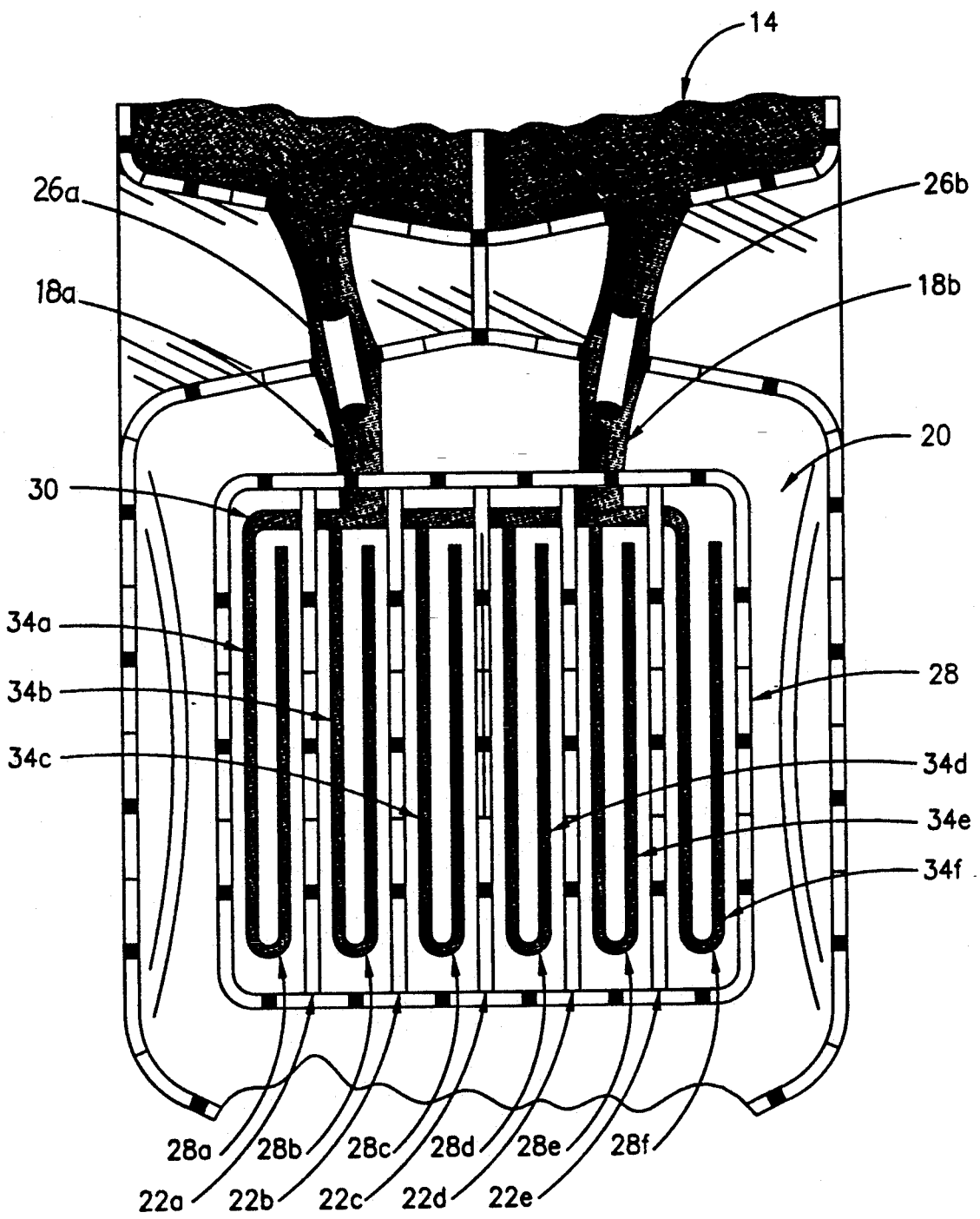
FIG. 4 is a side cross-sectional elevational view of an alternative embodiment for the first lower flexible bladder assembly of an infusion administration container of the present invention.

The first embodiment shown in FIGS. 2 and 3 is designed for relatively more rapid heat transfer (and therefore more rapid temperature increase), for use with all infusible physiologic fluids. A second embodiment shown in FIG. 4 is designed for relatively more gradual, uniform heat transfer as a preferred embodiment for use with whole blood, although it could be used with any other infusible physiologic fluids.

Figure 1:
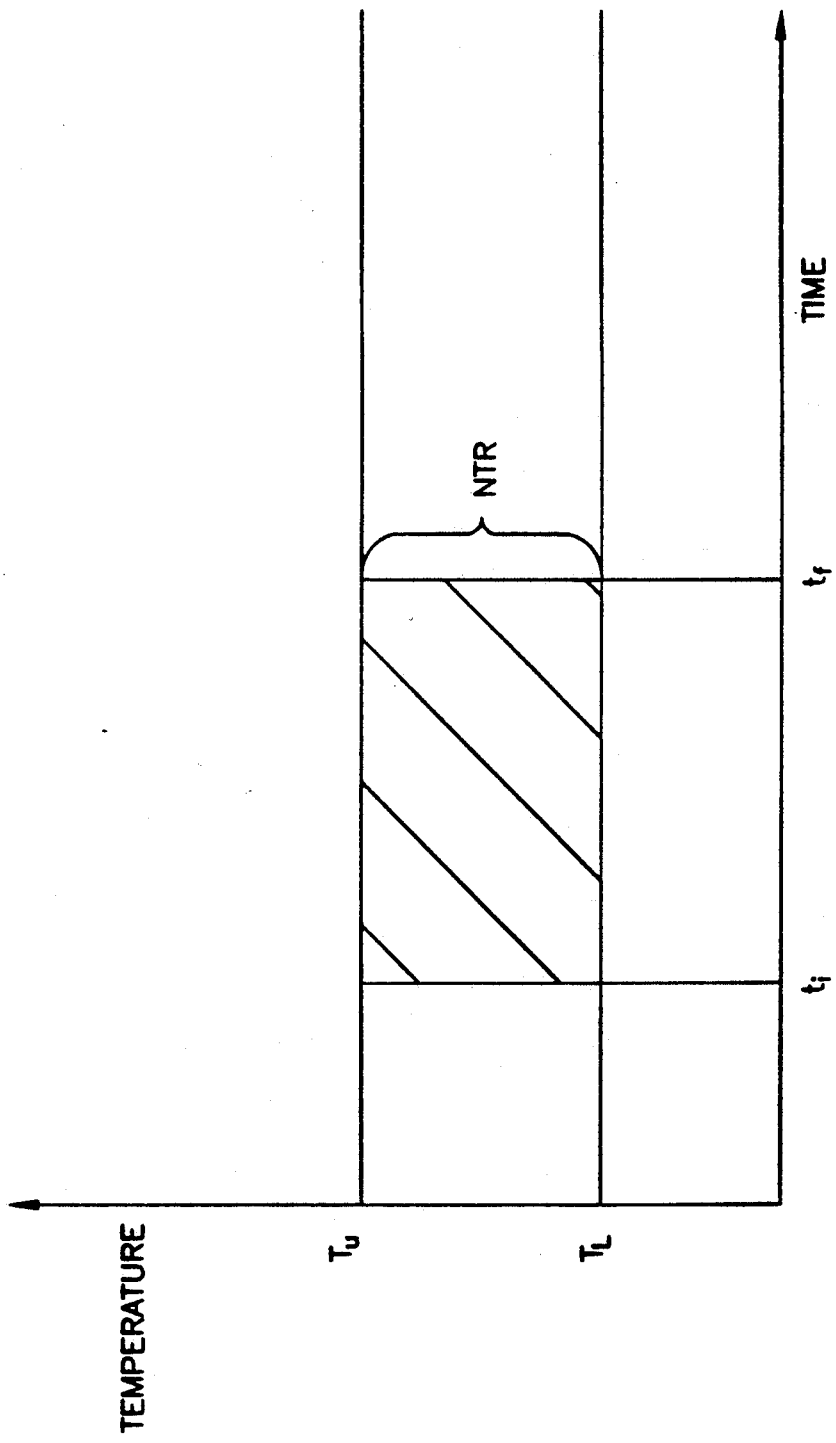
FIG. 1 depicts graphically the normothermic temperature range to be established in accordance with the invention as a function of time.

As can be seen by reference to FIG. 1, a normothermic temperature range ("NTR") is established between a lower temperature, $T_l$, and an upper temperature, $T_u$, within which the temperature of the physiologic fluid should be maintained during its infusion. Similarly, upon mixing of the chemical reactants at time zero, an exothermic chemical reaction will take an initial time (from time zero to time $t_i$) in order for the heat generated thereby to be transferred to the physiologic fluid so that its temperature is brought within the normothermic temperature range, in preparation for its infusion. The time for administration is the time between the administration is initiated, i.e. time $t_i$, and the time administration is completed, i.e. time $t_f$. This administration time depends upon the volume of the infused product and the flow rate established. During this infusion or administration time period, the temperature of the physiologic fluid should be maintained within the noted normothermic temperature range by virtue of the heat transferred from the chemical agents being reacted to the material being infused.

There are three rates which should be considered in constructing the device of the present invention and in practicing the method of the invention related to its use.

The first rate is the rate at which the chemical reactants are mixed and generate heat via exothermic reaction. The second rate is the rate of heat transfer from the reaction mixture to the physiologic fluid. The third rate is the rate at which the physiologic fluid will cool or, stated another way, how well the physiologic fluid will maintain its temperature once brought into the normothermic range.

The first rate will of course depend upon such things as the type (i.e. chemical and physical nature), amounts, volume, heat capacity and concentrations of the reactants. The second rate will depend upon such things as the thermal properties of the chemical agents and the physiologic fluid, the volumes of each, and the material and architecture of the device itself. The third rate will depend generally on the insulating nature of the materials used in the device, but will normally not be critical in instances where infusion occurs over a sufficiently short time so as not to allow time for substantial cooling.

Generally, with respect to heating to and maintaining the normothermic temperature range of the physiologic fluid, the heat of reaction dominates the other effects such as sensible heat effects or loss of heat to the environment.

For present purposes, it does not matter at what rate the temperature of the physiologic fluid reaches the normothermic temperature range, provided that degradation of the physiologic fluid does not occur as a result of the temperature exceeding a critical temperature as a result of too rapid a heating rate; and provided the heating rate is rapid enough to bring the physiologic fluid into the normothermic range as required in the particular infusion situation (e.g. faster rates for emergency administration). With specific regard to blood and blood products, it is important that the temperature not be allowed to exceed 42° C. at any time as such high temperatures can cause dangerous degradation of the blood or blood product. Conversely, most non-blood products are not so sensitive to higher temperatures and can tolerate spikes in temperature that may occur do to rapid initial reaction or non-uniform heat transfer.

Similarly, it does not matter whether the temperature of the physiologic fluid fluctuates within the normothermic temperature range during the administration of the physiologic fluid. It only is important that the temperature of the physiologic fluid is "maintained" within the normothermic temperature range, as set forth at FIG. 1. Desirably, the time period from the onset of the chemical reaction (point 0 in FIG. 1) to $t_i$ should be relatively short so that unnecessary delays in administration of the physiologic fluid do not result.

As will be observed by reference to FIG. 2, the infusion administration container of the present invention exhibits a design which allows it to function like conventional blood bags and similar medical fluid containers in the dispensing and infusion of physiologic fluids. Accordingly, upper tab 10 bears a centrally-disposed hole 11 for hanging the container on hook 12. The first and second chemical agents are retained respectively in upper flexible bladders 14a and 14b and first lower flexible bladder 16. These two flexible bladders are interconnected by passageway 18. Flexible bladders 14a and 14b and 16 are sealed from and do not provide material communication with second lower flexible bladder 20 in which is housed a volume of an administrable physiologic solution. The second lower flexible bladder, in turn, has lower disposed passageway 22 which is suitable for connection to hose 24 for setting up the administration container for infusion of the physiologic contained within lower flexible bladder 20.

Disposed within passageways 18a and 18b manually openable closure means 26a and 26b which serve to separate the two chemical agents disposed within bladders 14a and 14b and bladder 16. Such closure means can be broken or dislodged within passageways 18a and 18b for providing fluid communication between bladders 14a and 14b and bladder and 16. Note that closure means 26a and 26b can fall into bladder 16 conveniently to provide a full opening of passageways 18a and 18b. The configuration of the infusion administration container depicted at FIGS. 2 and 3 permit the, chemical agent housed within flexible bladders 14a and 14b to flow through passageway 18 into first lower flexible bladder 16 wherein the chemical agents combine. In some instances, however, a more controlled flow rate of the chemical agent from flexible bladders 14a and 14b, as it flows through passageway 18, is desired. Under such circumstances, reference is made to FIG. 4 described below, which provides an alternative embodiment for finer flow and reaction control.

Accordingly upper bladders such as 14a and 14b provide two or more bladder sections with individual closure means to allow the device to contain more than one first chemical agent portions which may differ in type, volume, combination and/or concentration. This allows a device to be constructed which allows the operator to select from among two or more different types, volumes, combinations and/or concentrations of the first chemical agent(s), to be able to control the amount of heat generated depending on the circumstances under which infusion is to be carried out. For instance, the operator might select from two or more different volumes of like concentrated chemical agent(s), from two or more concentrations of the chemical agent(s) at similar volumes, or from two types of chemical agents or agent combinations with varying reactivities toward the second chemical agent(s). Another way this embodiment of the present invention could be used is to have the operator use all of the bladder compartments sequentially to keep a heat-generating reaction going over time. This may be done, for instance, by having each of three compartments of the upper bladder contain one third the equivalent amount (of the first chemical agent(s)) to that of the second chemical agent(s) in the first lower bladder. The operator could then use each of the compartments' contents in sequence to maintain the reaction and prevent spikes in temperature, the latter advantage being particularly useful in the warming blood and blood products as discussed below.

Where whole blood is infused, the temperature should not be permitted to exceed that at which degradation (cell lysis or clotting) occurs (generally about 42° C.), in any portion of the blood to be infused. To this end, an alternative embodiment, specifically adapted for more gradual temperature increase, is shown in FIG. 4. First lower flexible bladder 28 is shown in an alternative embodiment in FIG. 4. It will be observed that lower flexible bladder 28 is divided into a series of sub-compartments 28a-28f. One or more chemical agents are housed within each sub-compartment 28a-28f and each said sub-compartment is in communication with upper flexible bladder 14 via passageway 18. Such communication is provided via manifold 30 which provides distribution into each said sub-compartment. A series of walls 22a–22e sub-divide lower flexible bladder 28 to provide such sub-compartments. Each distribution line from manifold 30 is formed into a U-shaped form with the terminal leg thereof containing a plurality of punctures or holes (shown as dots) which provide fluid communication into each sub-compartment 28a–28f. Such terminal U-shaped tubes are identified at 34a–34f. It will be appreciated that a lesser or greater number of sub-compartments, say ranging from 2–8, suitably could be provided.

The tortuous path created by the construction of bladder 28 depicted at FIG. 4 provides a series of reaction chambers for evening out the heat generated by the exothermic reaction being conducted therewithin when closure means 26 has been removed from passageway 18. Also, depending upon the size of the holes or orifices contained within tubes 34a–34f, the flow of chemical agent from upper flexible bladder 14 may be accomplished by gravity, or it may require a gentle squeezing of flexible bladder 14 to force chemical agent housed therewithin to flow into each sub-compartment 28a–28f. A more uniform that exchange results from such a bladder design.

As to the materials of construction, polyvinylchloride (PVC) o like flexible polymeric sheeting is the preferred material of construction for the administration container of the present invention. PVC sheeting or the like will provide a suitable oxygen barrier properties often required of the container, as well as safely housing both chemical agents, their reaction product(s), and the administrable physiologic fluid contained within lower flexible bladder 20. Finally, such material can be autoclaved for sterility of the administrable physiologic fluid.

As to the chemical agents, it will be appreciated that a variety of chemicals can be safely handled and reacted to provide the exothermic reaction required for maintaining the temperature of the administrable physiologic solution housed within second lower flexible bladder 20. Such materials may include those used to bring about a hydration reactions such as water as the first chemical agent and $MgSO_4$ as the second chemical agent; or acid/base reactions or the like. A more complete list of such exothermic reaction generating materials can be found by reference to Perry, *Chemical Engineers' Handbook*, 5th Ed., Table 3-204, McGraw-Hill Book Company, New York, N.Y. (1973), which is hereby incorporated herein by reference. While at least one of the chemical agents often will be provided in liquid form, it will be appreciated that a powdered or bead-like form may also be used, or one of the chemical agents can be encapsulated with a material which dissolves to release the chemical agent encapsulated therewithin. So long as the chemical reaction occurring generates sufficient heat, and is safe to use, such materials are suitable candidates for being employed in accordance with the precepts of the present invention.

The materials for construction of the container of the present invention should be chosen to separate the physiologic fluid from the chemical agents. Also, the second lower bladder 16 should be provided at a distance from passageway 22 greater than the length of the needle used to access the contents of bladder 20, if a needle is used.

With respect to selection of particular chemical agents, it will be appreciated that the mass of each agent is a function of its density and volume in accordance with the following mathematical relationship:

$$M = rho \cdot V, \tag{1}$$

where
  $M$ = mass of reactant,
  rho = density of reactant, and
  $V$ = volume of reactant.

The heat generated by the reaction is a function of the mass of the agents, and the heat released by the reaction on a per mass basis, in accordance with the following mathematical relationship:

$$Q = M \cdot delta\ H_{rxn}, \tag{2}$$

where:
  $Q$ = heat generated,
  $M$ = mass of the limiting reactants,
  delta $H_{rxn}$ = heat released by the reaction.

Thus, it will be seen that the heat generated by the chemical reaction is proportional to the volume of the chemical reactants established. For convenience, for efficiency of heat transfer, and for conventional volumes of physiologic fluids, it is desirable that the volume of the chemical reactants be minimized and the heat generated by their reaction be maximized. The minimization of volume and maximization of exothermic heat can be regulated by the selection of appropriate reactants with due regard to their densities and the heat of reaction of the reactant combination.

As to the physiologic fluids suitable for use in the present invention, such fluids may include blood and blood products, non-blood materials such as crystalloids, drugs, saline solutions, dextrose and glucose solutions, Lactated Ringers solution, and the like. Non-blood materials often are stored at ambient temperature so that the amount of heat required for such physiologic solutions depends upon the ambient conditions of storage which, in turn, depend upon the climate of the locale, and the season. Blood and blood products, in contrast, generally are stored at about 5°–15° C. For blood products, then, a greater amount of heat per unit volume often is required in order to raise the temperature thereof. For non-blood materials having an initial temperature typically ranging from about 15°–30° C., the ultimate temperature range desired is a normothermic range, which, for most applications, is a temperature range of from about 32° to about 42° C., and preferably in the range of normal body temperatures. With blood and blood products, great care must be taken that the temperature is not raised above about 42° C.; otherwise, degradation of the red blood cells or clotting will occur.

Because it is desirable to bring the temperature of the administrable physiologic fluid efficiently to within the normothermic range, the method of the present invention, following opening of the closure means, preferably involves agitation of the container, or more accurately the contents within the container including the physiologic fluid, the reactants, and the reaction product being formed in the lower flexible bladder. Most easily, such agitation is accomplished by the hand of a person involved in the administration operation. Agitation from gentle rocking back and forth to vigorous shaking facilitates good mixing of the chemical agents for encouraging complete reaction, ensuring uniform heat generation therefrom; and to better provide uniform heat transfer to the physiologic fluid. The upper flexible bladder 14 can also be gently squeezed to force the first chemical agent into the first lower flexible bladder such as depicted at FIG. 3, while agitating the contents of the infusion administration container.

The following examples show how the present invention has been practiced, but should not be construed as limiting. In this application, all citations are expressly incorporated herein by reference.

EXAMPLES

Example 1

In order to verify the controlled heating of infusates in conventional PVC infusion bags, a test was run using a device as shown in FIGS. 2 and 3, which is adapted from a commercially available dual bladder infusion bag. This bag was filled with 1,000 ml of water as the infusate, and with 125 ml of water and 45 ml of $MgSO_4$ power (120 g) as the first and second chemical agents, respectively. All of the $MgSO_4$ and water were mixed and the temperatures of the reaction mixture and the infusate recorded. The reaction mixture was agitated by hand in order to stimulate the reaction and to aid in heat exchange.

The underlying principles of heat transfer in such a system are well known in the chemical and physical arts, and may be understood by reference to any appropriate text, such as Incropera and DeWitt, *Introduction to Heat Transfer*, 2nd Edition, Wiley & Sons (1990), which is hereby incorporated herein by reference. The calculations relating to the generation, absorption, and transfer of heat in such a system may be made by reference to equations and relationships well known in the art, and may be found in may texts including Myers, *Analytical Methods in Conduction*, McGraw-Hill (1971), which is hereby incorporated herein by reference. Such calculations may be done using well known values relevant thereto and specific values such as those given above.

Figure 5:
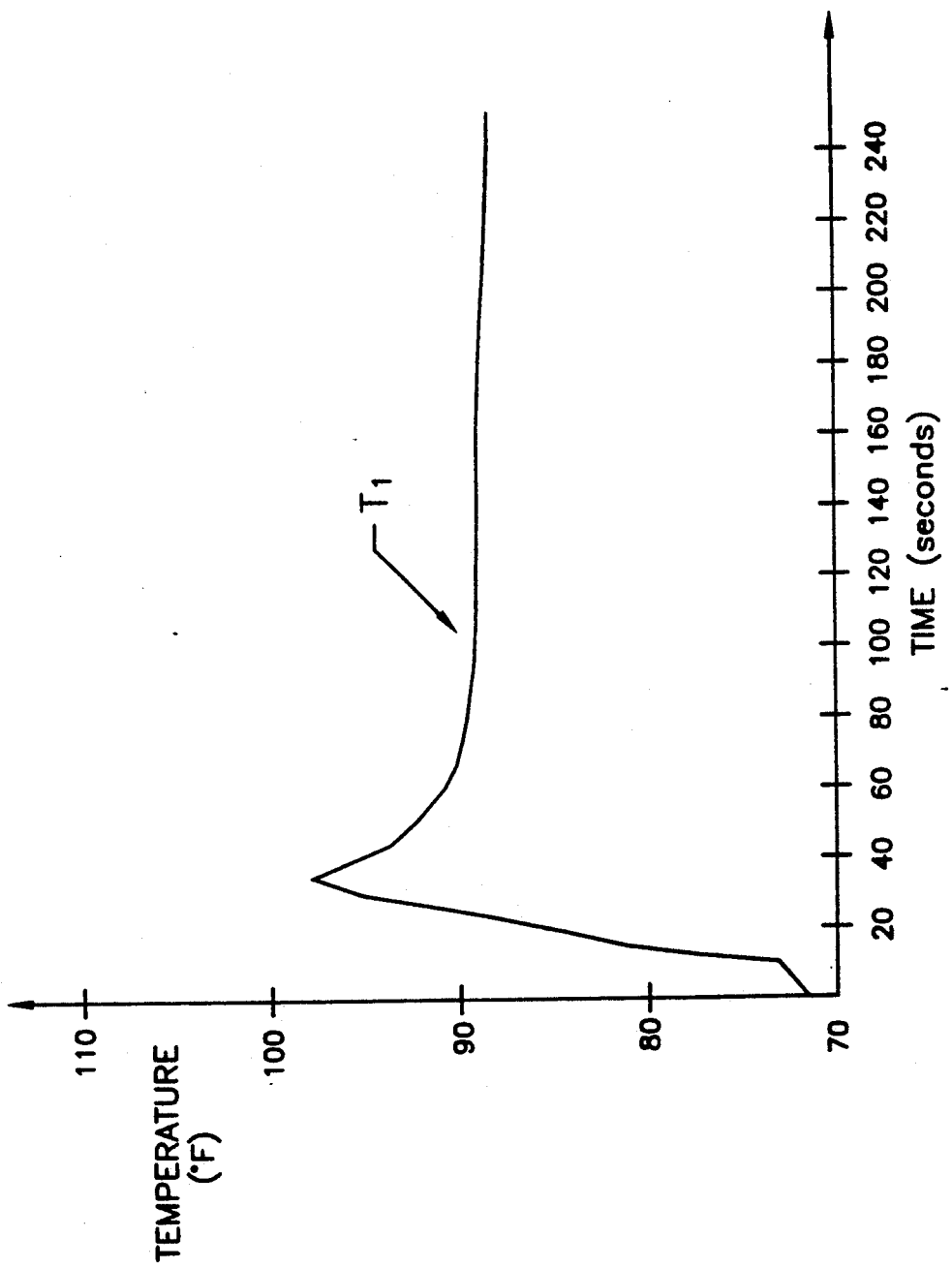
FIG. 5 depicts graphically the results reported in Example 1.

The results of this test are set forth at FIG. 5 wherein $T_1$ represents the temperature of the infusate (i.e. water used as a test infusate in this example). It will be observed that after about 20-25 seconds following initiation of the reaction, the temperature of the infusate was within the desired range of 32°-37° C. In fact, the temperature of the infusate was maintained above the minimum normothermic temperature for about 4 minutes.

It will be observed that the heated infusate was brought to and maintained within a normothermic temperature range in a controlled manner. Again, it is demonstrated that the temperature of the exothermic reaction mixture may fluctuate, and such fluctuation does not detract from the efficacy of the procedure, so long as the solution to be administered is brought to within and/or maintained within the appropriate temperature range, i.e. normothermic temperature range.

In accordance with the foregoing description of the present invention, it will be obvious to one of ordinary skill to make alterations, modifications and substitutions, using equivalent materials and arrangements in the present invention without departing from its spirit and purpose.

What is claimed is:

1. An infusion administration container for infusing a physiologic fluid into an animal, which comprises:
    a first flexible bladder divided into at least two compartments separated from one another, each of said compartments containing at least one first chemical agent;
    a second flexible bladder disposed outside said first flexible bladder and containing at least one second chemical agent, said first and second chemical agents when combined resulting in an exothermic reaction;
    passageways interconnecting each of said compartments of said first bladder with said second bladder;
    manually openable closure means disposed within each of said passageways;
    a third flexible bladder adapted to contain an administrable physiologic fluid and being in a contacting heat-exchange relationship with said second bladder, said first and second chemicals provided in amounts sufficient and said passageways being dimensioned such that when said closure means is opened, said at least one first chemical agent flows into said second flexible bladder at a rate sufficient so that the resulting exothermic reaction with said at least one second chemical agent generates sufficient heat to maintain said physiologic fluid at about 32 degrees to 42 degrees Centigrade for its infusion into said animal; and
    fluid conduction means adapted to conduct said physiologic fluid into said animal.

2. The infusion administration container of claim 1 wherein one of said at least one first or at least one second chemical agents comprises water and the other of said at least one second or at least one first chemical agents, respectively, comprises a hydratable compound.

3. The infusion administration container of claim 2 wherein said hydratable compound comprises magnesium sulfate.

4. The infusion administration container of claim 1 wherein one of said at least one first or at least one second chemical agents comprises an acid and the other of said at least on second or at least one first chemical agents, respectively, comprises a base.

5. The infusion administration container of claim 1 wherein said compartments of said first flexible bladder each contain said at least one first chemical agent wherein said at least one first chemical agent contained in each of said compartment differs from said at least one first chemical agent in the respective other of said compartments, with respect to a characteristic selected from the group consisting of: (a) chemical nature, (b) physical form, (c) concentration, and (d) volume; and wherein said first lower bladder contains said at least one second chemical agent.

6. The infusion, administration container of claim 1 wherein said second flexible bladder is disposed within said third flexible bladder.

7. The infusion administration container of claim 1 wherein said second flexible bladder is subdivided into a plurality of chambers.

8. The infusion administration container of claim 7 wherein said plurality of chambers comprises between 2 and 8 of said chambers.

9. The infusion administration container of claim 1 wherein said infusion administration container is made from a material selected from the group consisting of polyvinylchlorides.

10. A method for maintaining a physiologic fluid at about a normothermic temperature for its infusion into an animal which comprises the steps of:
    (a) providing an infusion administration container which comprises a first flexible bladder divided into at least two compartments separated from one another, each of said compartments containing at least one first chemical agent, a second flexible bladder disposed outside said first flexible bladder and containing at least one second chemical agent wherein said first and second chemical agents when combined result in an exothermic reaction; there being passageways interconnecting each of said compartments of said first flexible bladder and said second bladder, with manually openable closure means disposed within each of said passageways to separate said at least one first chemical agent in each of said compartments of said first flexible bladder from said at least one second chemical agent until each said closure means is opened, said closure means thereby comprising a series of said closure means, and a third flexible bladder containing an administrable physiologic fluid, and said third flexible bladder being in a contacting heat exchange relationship with said second flexible bladder and said third flexible bladder containing fluid conduction means adapted to conduct said physiologic fluid into said animal; and (b) opening each said closure means of said series in sequence, so that the resulting exothermic reaction generates sufficient heat to maintain the physiologic fluid at about 32 degrees to 42 degrees Centigrade for its infusion into said animal; and 'allowing said physiologic fluid to flow through said fluid conduction means into said animal.

11. The method of claim 10 additionally comprising the step of agitating said container upon said opening of said closure means and during said infusion into said animal.

12. The method of claim 10 wherein one of said at least one first or at least one second chemical agents comprises water and the other of said at least one second or at least one first chemical agents, respectively, comprises a hydratable compound.

13. The method of claim 12 wherein said hydratable compound comprises magnesium sulfate.

14. The method of claim 10 wherein one of said at least one first or at least one second chemical agents comprises an acid and the other of said at least one second or at least one first chemical agents, respectively, comprises a base.

15. The method of claim 10 wherein said first lower flexible bladder is disposed within said second lower flexible bladder.

16. The method of claim 10 wherein said second flexible bladder is subdivided into a plurality of chambers.

17. The method of claim 16 wherein said plurality of chambers comprises between 2 and 8 of said chambers.

18. The method of claim 10 which is made from a material selected from the group consisting of polyvinylchlorides.

19. An infusion administration container according to claim 1 wherein said container additionally comprises attachment means whereby said container may be suspended by said attachment means such that said first flexible bladder is held in a position above said second flexible bladder.

* * * * *